United States Patent
Pevarello et al.

[11] Patent Number: 6,133,302
[45] Date of Patent: Oct. 17, 2000

[54] 5-(3-PHENYL-3-OXO-PROPYL)-1H-TETRAZOLE DERIVATIVES

[75] Inventors: Paolo Pevarello; Antonio Giordani, both of Pavia; Manuela Villa, Lurago d'Erba; Carmela Speciale, Nerviano; Mario Varasi, Milan, all of Italy

[73] Assignee: Pharmacia & Upjohn SpA, Milan, Italy

[21] Appl. No.: 09/446,895

[22] PCT Filed: Jun. 25, 1998

[86] PCT No.: PCT/EP98/04032

§ 371 Date: Dec. 30, 1999

§ 102(e) Date: Dec. 30, 1999

[87] PCT Pub. No.: WO99/02506

PCT Pub. Date: Jan. 21, 1999

[30] Foreign Application Priority Data

Jul. 7, 1997 [GB] United Kingdom .................. 9714303

[51] Int. Cl.⁷ ......................... A61K 31/41; C07D 257/04
[52] U.S. Cl. ............................. 514/381; 548/253
[58] Field of Search .............. 548/253; 514/381

[56] References Cited

U.S. PATENT DOCUMENTS 4,764,521  8/1988  Herron ..................................... 514/381

FOREIGN PATENT DOCUMENTS 0 014 847   9/1980   European Pat. Off. .
95 11878    5/1995   WIPO .

*Primary Examiner*—Laura L. Stockton
*Attorney, Agent, or Firm*—Arent Fox Kintner Plotkin & Kahn, PLLC

[57] ABSTRACT

5-(3-phenyl-3-oxo-propyl)-1H-tetrazole derivatives of formula (I) wherein each of R and $R_1$, being the same or different, is hydrogen, halogen, hydroxy, trifluoromethyl, cyano, nitro, phenyl, benzyl, $C_1$–$C_6$ alkyl, $C_1$–$C_6$ alkoxy, $C_1$–$C_6$ alkylthio, $SOR_4$ or $SO_2R_4$ wherein $R_4$ is $C_1$–$C_6$ alkyl, —$N(R_5R_6)$ in which each of $R_5$ and $R_6$ is, independently, hydrogen, $C_1$–$C_6$ alkyl, formyl or $C_2$–$C_6$ acyl; $R_2$ is hydrogen, $C_1$–$C_6$ alkyl, $C_1$–$C_6$ alkoxy, benzyl, phenyl; $R_3$ is hydrogen, hydroxy, $C_1$–$C_6$ alkyl, $C_1$–$C_6$ alkoxy, benzyl, phenyl or a group —$N(R_7R_8)$ in which each of $R_7$ and $R_8$ is, independently, hydrogen, $C_1$–$C_4$ alkyl, benzyl, phenyl, or one of $R_7$ and $R_8$ is hydrogen and the other is $COR_9$ wherein $R_9$ is hydrogen, $C_1$–$C_4$ alkyl, $C_1$–$C_4$ alkoxy, phenyl or a group —$N(R_{10}R_{11})$ in which $R_{10}$ and $R_{11}$ are, each independently, hydrogen or $C_1$–$C_4$ alkyl or, taken together, $R_2$ and $R_3$ form a carbocyclic $C_3$–$C_6$ ring; and pharmaceutically acceptable salts thereof have kynurenine-3-hydroxylase enzyme inhibitory activity.

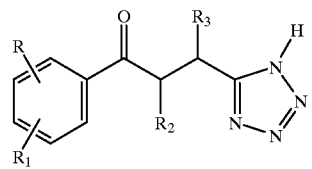

7 Claims, 1 Drawing Sheet

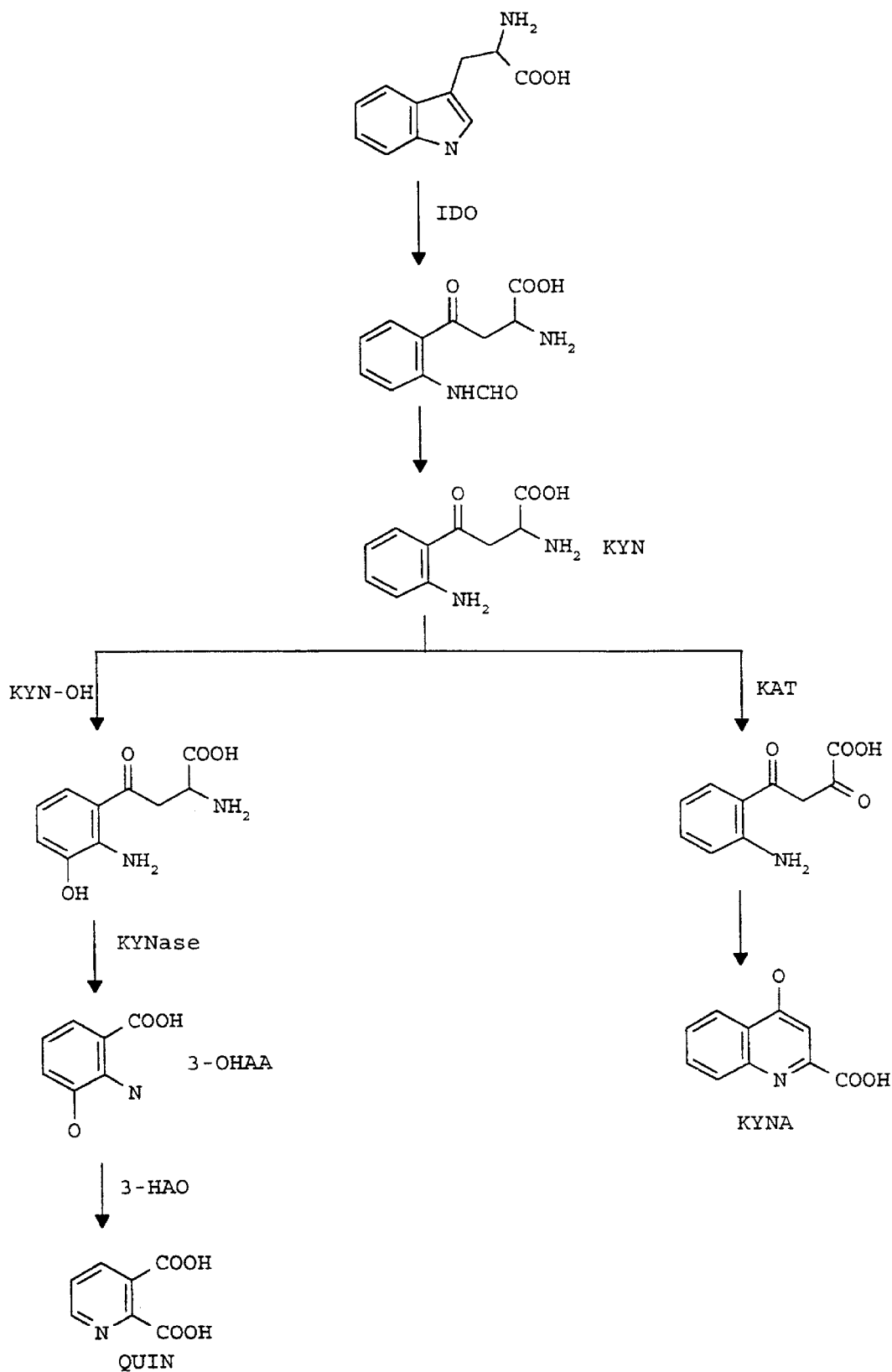

5-(3-PHENYL-3-OXO-PROPYL)-1H-TETRAZOLE DERIVATIVES

This application is a 371 of PCT/EP98/04032 filed Jun. 25, 1998.

The present invention relates to 5-(3-phenyl-3-oxo-propyl)-1H-tetrazole derivatives, to a process for their preparation, to pharmaceutical compositions containing them and to their use in therapy.

The compounds of the invention are inhibitors of Kynurenine-3-hydroxylase (KYN-OH), an enzyme which is involved in the metabolic pathway of kynurenine.

BRIEF DESCRIPTION OF DRAWING

It is well known in the art that through the kynurenine pathway, tryptophan metabolism gives rise to the formation of both 3-hydroxykynurenine(3-OHKYN) and quinolinic acid (QUIN) on the one side, and kynurenic acid (KYNA) on the other side, as shown in FIG. 1. (The legend to FIG. 1 has to be found on the last page of the experimental part of the specification).

Both KYNA and QUIN are known to possess biological activities. KYNA, in particular, is endowed with neuroprotective properties (J. Neurosci. 1990,10,2965–2973), whereas QUIN is a potent neurotoxin which has been implicated in the pathogenesis of a variety of neurological disorders (Life Sci. 1984,35,19–32; Nature, 1986,321, 168–171; Science, 1983,219,316–318).

Increasing concentrations of QUIN have also been indicated as responsible of neurological disorders accompanying many infections and inflammatory diseases including Acquired Immunodeficiency Syndrome (AIDS) (Ann. Neurol. 1991,29,202–209).

One of the main strategies aimed at altering the KYNA/QUIN balance, either blocking 3-OHKYN and QUIN's production or increasing KYNA production, entails the inhibition of the key enzymes of kynurenine (KYN) pathway among which, particularly relevant is Kynurenine-3-hydroxylase.

Consequently, there is a need in therapy of compounds enabling the inhibition of said enzyme.

We have surprisingly found that some derivatives of 5-(3-phenyl-3-oxo-propyl)-1H-tetrazole, being endowed with inhibitory activity towards Kynurenine-3-hydroxylase, fulfil such a need.

Accordingly, the present invention provides a compound which is a 5-(3-phenyl-3-oxo-propyl)-1H-tetrazole derivative of formula (I)

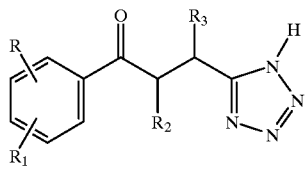

(I)

wherein
each of R and $R_1$, being the same or different, is hydrogen, halogen, hydroxy, trifluoromethyl, cyano, nitro, phenyl, benzyl, $C_1$–$C_6$ alkyl, $C_1$–$C_6$ alkoxy, $C_1$–$C_6$ alkylthio, $SOR_4$ or $SO_2R_4$ wherein $R_4$ is $C_1$–$C_6$ alkyl, —$N(R_5R_6)$ in which each of $R_5$ and $R_6$ is, independently, hydrogen, $C_1$–$C_6$ alkyl, formyl or $C_2$–$C_6$ acyl;

$R_2$ is hydrogen, $C_1$–$C_6$ alkyl, $C_1$–$C_6$ alkoxy, benzyl, phenyl;

$R_3$ is hydrogen, hydroxy, $C_1$–$C_6$ alkyl, $C_1$–$C_6$ alkoxy, benzyl, phenyl or a group —$N(R_7R_8)$ in which each of $R_7$ and $R_8$ is, independently, hydrogen, $C_1$–$C_4$ alkyl, benzyl, phenyl, or one of $R_7$ and $R_8$ is hydrogen and the other is $COR_9$ wherein $R_9$ is hydrogen, $C_1$–$C_4$ alkyl, $C_1$–$C_4$ alkoxy, phenyl or a group —$N(R_{10}R_{11})$ in which $R_{10}$ and $R_{11}$ are, each independently, hydrogen or $C_1$–$C_4$ alkyl or, taken together, $R_2$ and $R_3$ form a carbocyclic $C_3$–$C_6$ ring; or a pharmaceutically acceptable salt thereof;

for use as a Kynurenine-3-hydroxylase inhibitor.

In the present description, the alkyl and alkoxy groups of the compounds of formula (I) may be branched or straight groups.

Representative examples of $C_1$–$C_6$ alkyl groups include $C_1$–$C_4$ alkyl groups such as methyl, ethyl, n- and isopropyl, n-, iso-, sec- and tert-butyl groups.

Representative examples of $C_1$–$C_6$ alkoxy groups include $C_1$–$C_4$ alkoxy groups such as methoxy or ethoxy.

Representative examples of $C_1$–$C_6$ alkylthio groups include $C_1$–$C_4$ alkylthio groups such as methylthio or ethylthio groups.

Representative examples of $C_1$–$C_6$ acyl groups include $C_1$–$C_4$ acyl groups such as acetyl or propionyl.

Representative examples of $C_1$–$C_6$ alkoxycarbonyl groups include $C_1$–$C_4$ alkoxycarbonyl groups such as methoxycarbonyl or ethoxycarbonyl groups.

A halogen atom is fluorine, bromine, chlorine or iodine; being chlorine or fluorine particularly preferred.

Pharmaceutically acceptable salts of the compounds of formula (I) are the acid addition salts with inorganic, e.g. nitric, hydrochloric, hydrobromic, sulphuric, perchloric and phosphoric acid or organic, e.g. acetic, trifluoroacetic, propionic, glycolic, lactic, oxalic, malonic, malic, maleic, tartaric, citric, benzoic, cinnamic, mandelic and salicylic acid, as well as the salts with inorganic bases, e.g. alkali or alkaline-earth metals, especially sodium, potassium, calcium or magnesium hydroxides, carbonates or bicarbonates, or with organic bases, e.g. acyclic or cyclic amines, preferably methylamine, ethylamine, diethylamine, triethylamine or piperidine.

The compounds of formula (I) may have asymmetric carbon atoms and may therefore exist either as racemic mixtures or as individual optical isomers. Moreover, the compounds of the invention can also be as (E) or (Z) isomers or as mixtures thereof.

Accordingly, the use as Kynurenine-3-hydroxylase inhibitors of all the possible isomers and their mixtures and of both the metabolites and the pharmaceutically acceptable bioprecursors (otherwise known as pro-drugs) of the compounds of formula (I) are also within the scope of the present invention.

The present invention further provides the use of a 5-(3-phenyl-3-oxo-propyl)-1H-tetrazole derivative of formula (I) as defined above, or a pharmaceutically acceptable salt thereof, in the preparation of a medicament having Kynurenine-3-hydroxylase inhibitory activity. Among the compounds of formula (I) above reported, several 5-(3-phenyl-3-oxo-propyl)-1H-tetrazole derivatives result to be novel.

Therefore, the present invention further provides a compound which is a 5-(3-phenyl-3-oxo-propyl)-1H-tetrazole derivative of formula (Ia)

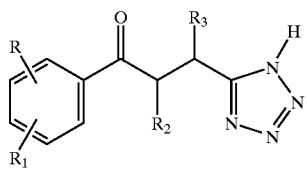

(Ia)

wherein
each of R and $R_1$, being the same or different, is hydrogen, halogen, trifluoromethyl, cyano, nitro, benzyl, $C_1$–$C_6$ alkylthio, $SOR_4$ or $SO_2R_4$ in which $R_4$ is $C_1$–$C_6$ alkyl, —$N(R_5R_6)$ in which each of $R_5$ and $R_6$ is, independently, hydrogen, $C_1$–$C_6$ alkyl, formyl or $C_2$–$C_6$ acyl;

$R_2$ is hydrogen, $C_1$–$C_6$ alkyl, $C_1$–$C_6$ alkoxy, benzyl, phenyl;

$R_3$ is hydrogen, hydroxy, $C_1$–$C_6$ alkyl, $C_1$–$C_6$ alkoxy, benzyl, phenyl or a group —$N(R_7R_8)$ in which each of $R_7$ and $R_8$ is, independently, hydrogen, $C_1$–$C_4$ alkyl, benzyl, phenyl, or one of $R_7$ and $R_8$ is hydrogen and the other is $COR_9$ wherein $R_9$ is hydrogen, $C_1$–$C_4$ alkyl, $C_1$–$C_4$ alkoxy, phenyl or a group —$N(R_{10}R_{11})$ in which $R_{10}$ and $R_{11}$ are, each independently, hydrogen or $C_1$–$C_4$ alkyl or, taken together, $R_2$ and $R_3$ form a carbocyclic $C_3$–$C_6$ ring; or a pharmaceutically acceptable salt thereof.

Also for the compounds of formula (Ia), unless otherwise specified, with the term alkyl, alkoxy, alkylthio, acyl or alkoxycarbonyl groups or halogen atoms, we intend the groups above reported for the compounds of formula (I).

Likewise, all possible optical or geometric isomers (E,Z) as well as the pharmaceutically acceptable salts of the compounds of formula (Ia) are within the scope of the present invention.

Preferred compounds of the invention are the compounds of formula (Ia) wherein:
each of R and $R_1$, being the same or different, is hydrogen, halogen, trifluoromethyl;

$R_2$ is hydrogen, $C_1$–$C_4$ alkyl, $C_1$–$C_4$ alkoxy, benzyl, phenyl;

$R_3$ is hydrogen, hydroxy, $C_1$–$C_6$ alkyl, $C_1$–$C_6$ alkoxy, benzyl, phenyl, or a group —$N(R_7R_8)$ in which each of $R_7$ and $R_8$ is, independently, hydrogen, $C_1$–$C_4$ alkyl, benzyl, phenyl, or one of $R_7$ and $R_8$ is hydrogen and the other is $COR_9$ in which $R_9$ is hydrogen, $C_1$–$C_4$ alkyl, $C_1$–$C_4$ alkoxy, phenyl or a group —$N(R_{10}R_{11})$ in which $R_{10}$ and $R_{11}$ are hydrogen or $C_1$–$C_4$ alkyl or, taken together, $R_2$ and $R_3$ form a carbocyclic $C_3$–$C_6$ ring; and the pharmaceutically acceptable salts thereof.

Still more preferred compounds, in this class, are the compounds of formula (Ia) wherein R and $R_1$ are both halogen atoms.

Examples of preferred compounds of the invention, as single (E) or (Z) isomers or mixtures thereof, as single optical isomers or mixtures thereof and, whenever appropriate, in the form of pharmaceutically acceptable salts, are the following compounds:

5-[3-(3-fluorophenyl)-3-oxo-propyl]-1H-tetrazole;
5-[3-(3-chlorophenyl)-3-oxo-propyl]-1H-tetrazole;
5-[3-(3-bromophenyl)-3-oxo-propyl]-1H-tetrazole;
5-[3-(3,4-dichlorophenyl)-3-oxo-propyl]-1H-tetrazole;
5-[3-(3,4-difluorophenyl)-3-oxo-propyl]-1H-tetrazole;
5-[1-benzyl-3-(3,4-dichlorophenyl)-3-oxo-propyl]-1H-tetrazole;
1-(3,4-dichlorobenzoyl)-2-(1H-tetrazol-5-yl)-cyclopropane;
1-(3,4-difluorobenzoyl)-2-(1H-tetrazol-5-yl)-cyclopropane.

The compounds of formula (Ia), of the present invention, as well as the whole group of compounds of formula (I), are therapeutically active substances, in particular as kynurenine-3-hydroxylase enzyme inhibitors and are thus useful in the prevention and/or treatment of neuropathological processes including, e.g. Huntington's chorea, Alzheimer's disease, Parkinson's disease and other related neurodegenerative disorders.

A further object of the present invention are thus the pharmaceutical compositions comprising a therapeutically effective amount of a compound of formula (Ia).

The present invention also provides a method of treating a mammal, including a human, in need of a kynurenine-3-hydroxylase inhibitor, such a method comprising administering thereto a therapeutically effective amount of a compound of formula (I), as defined above, or a pharmaceutically acceptable salt thereof.

The compounds of formula (Ia) object of the present invention and the salts thereof can be obtained, for instance, by a process comprising:

a) reacting a compound of formula (II)

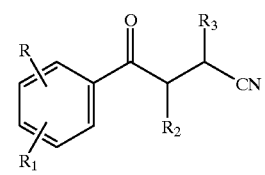

(II)

wherein R, $R_1$, $R_2$ and $R_3$ are as defined above, with a trialkyl tin azide, or b) reacting a compound of formula (III)

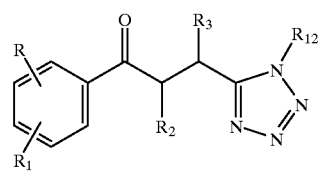

(III)

wherein R, $R_1$, $R_2$ and $R_3$ are as defined above and $R_{12}$ is a substituted benzyl group, with a suitable hydrolysing agent; and, c) if desired, converting a compound of formula (Ia) into a pharmaceutically acceptable salt.

The above process-variants a) and b) are analogy processes which can be carried out according to well know methods in the art.

The reaction of a compound of formula (II) with a trialkyl tin azide can be carried out, for example, by using tri(n-butyl)tin azide in a suitable solvent such as, toluene, at a temperature ranging from about −78° C. to about 150° C., for a time of from about 1 hour to ten days.

The optional salification of the compounds of formula (Ia) thus obtained, as well as the conversion of an addition salt into the corresponding free compound, and the separation into the single isomers of the mixtures thereof, may all be accomplished by conventional methods.

As stated above, the compounds (Ia) of the invention may have asymmetric carbon atoms and (E,Z) isomerism. Accordingly, they can be prepared either as a mixture to be subsequently separated according to conventional techniques, or as single isomeric compounds by well-known stereospecific processes.

The compound of formula (II), as defined above, can be obtained for instance by reacting a compound of formula (IV)

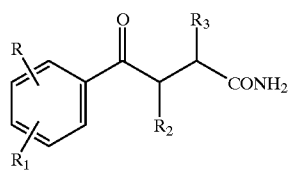

(IV)

wherein R, $R_1$, $R_2$ and $R_3$ are as defined above, with a suitable dehydrating agent such as, for instance, phopsphoryl chloride, in a suitable solvent such as DMF, at a suitable temperature, e.g. from −20° C. to 100° C., for a time comprised between 1 to 24 hours.

The compounds of formula (IV), in their turn, can be obtained by reacting a corresponding compound of formula (V)

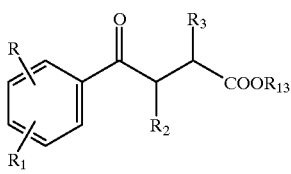

(V)

wherein $R_{13}$ is a $C_1$–$C_4$ alkyl group, usually a methoxy group, with ammonia in a suitable solvent such as 1,4-dioxane, at a suitable temperature, e.g. from −20° C. to 100° C., for a suitable time, e.g. from 1 hour to few days.

The compounds of formula (V), as starting materials, are known compounds or can be easily prepared according to known methods.

Alternatively, the compounds of formula (II) can be prepared by heating the compounds of formula (VI)

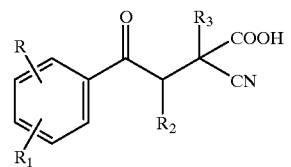

(VI)

wherein R, $R_1$, $R_2$ and $R_3$ are as defined above; in a suitable solvent such as 1,4-dioxane, at a suitable temperature, e.g. from 78° C. to 180° C., for a suitable time, e.g. from 1 hour to few days.

The compounds of formula (VI) can be obtained by a multi-step process comprising the reaction of a compound of formula (VII)

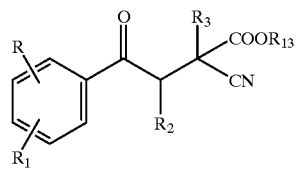

(VII)

wherein $R_1$, $R_2$, $R_3$ and $R_{13}$ are as defined above, with an alkali agent.

The compounds of formula (VII) can be obtained by reacting a compound of formula (VIII)

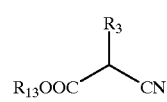

(VIII)

wherein $R_3$ and $R_{13}$ have the meanings above reported, with a compound of formula (IX)

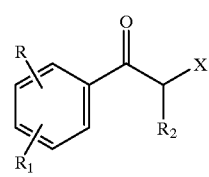

(IX)

wherein X is a halogen atom.

The reaction of a compound of formula (VII) to obtain a compound of formula (VI) can be accomplished by basic hydrolysis, i.e. by using an alcoholic solution of an alkali metal hydroxide, typically a sodium hydroxide solution in a suitable alcoholic medium, i.e. methanol, at a suitable temperature, e.g. between 0° C. and 55° C., for a suitable time, e.g., 2–24 hours.

The reaction of a compound of formula (VIII) with a compound of formula (IX) to obtain a compound of formula (VII) can be accomplished by using an anhydrous solution of an alkaline alcoholate, e.g. sodium ethylate, at a temperature ranging between −20° C. and 78° C., for a time ranging between 1 and 48 hours.

The compounds of formula (VIII) and (IX) are known compounds or can be easily prepared according to known methods.

A compound of formula (III) according to process-variant b) can be obtained by a multi-step process comprising reacting a compound of formula (X)

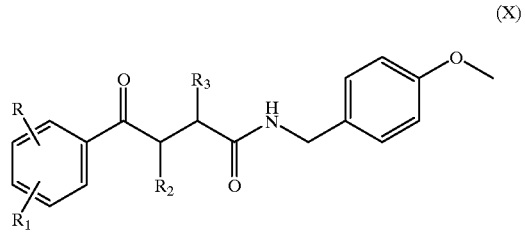

(X)

wherein R, $R_1$, $R_2$ and $R_3$ have the above reported meanings, with an alkali azide.

The compounds of formula (X) can be obtained from a compound of formula (XI)

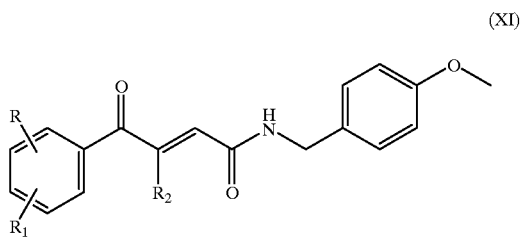

(XI)

wherein R, $R_1$ and $R_2$ are as defined above, by treatment with a suitable derivative of general formula (XII)

$$R_3—M \quad (XII)$$

wherein $R_3$ has the above reported meanings and M is a hydrogen atom or an alkali metal such as lithium or sodium. The compounds of formula (XI) can be obtained by amidation of the corresponding compounds of formula (XIII)

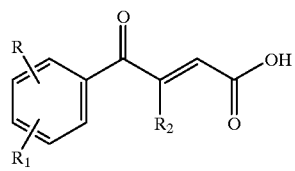

(XIII)

wherein R, $R_1$ and $R_2$ have the above reported meanings.

The conversion of a compound of formula (X) into a compound of formula (III) can be accomplished, for instance, by using azidotrimethylsilane, in the presence of DEAD and triphenylphosphine, in a suitable solvent, e.g. THF, at a suitable temperature, e.g. between $-20°$ C. and $110°$ C. for a suitable time, ranging between 1 hour and few days.

The conversion of a compound of formula (XI) into a compound of formula (X) can be accomplished in a suitable solvent, e.g. THF at a suitable temperature, e.g. between $-78°$ C. and $110°$ C., for a suitable time, ranging between 0.5 and 48 hours.

The conversion of a compound of formula (XIII) to give a compound of formula (XI) can be accomplished by using 4-methoxybenzylamine in a suitable solvent, such as dichloromethane at a suitable temperature, e.g. between $-78°$ C. and $110°$ C. for a suitable time, e.g. 1–72 hours. Compounds of formula (XII) and (XIII) are known compounds or can be prepared according to known methods reported in the literature.

It is clear to the man skilled in the art that whenever are present functional groups which could interfere in the reaction, either in the starting materials or in the intermediates for the preparation of the compounds of formula (Ia), said groups need to be protected before the reaction takes place and then deprotected at the end of the reaction.

For instance, hydroxy, amino and/or carboxy groups may be protected and then deprotected according to the commonly known techniques of the chemistry of peptides.

It is also clear to the man skilled in the art that the processes above described for the preparation of the compounds of formula (Ia), object of the present invention, can be applied as well to the preparation of the whole group of compounds of formula (I).

PHARMACOLOGY

The compounds of formula (I), whose formula also encompasses those of formula (Ia), are active as kynurenine-3-hydroxylase enzyme inhibitors and are therefore useful in the prevention and/or treatment of neuropathological processes related to a deranged production of quinolinic acid and/or 3-hydroxykynurenine, due to an excessive activation of the neuro-transmission mediated by excitatory amino acid receptors and/or oxidative stress. Examples of such neuropathological processes are neurodegenerative pathologies including, e.g. Huntington's chorea, Alzheimer's disease, Parkinson's disease, olivoponto cerebral atrophy, non-Alzheimer's dementias, including the dementia like syndrome caused by Acquired Immunodeficiency Syndrome (AIDS), multi-infarctual dementia, cerebral amyotrophic lateral sclerosis, cerebral ischemia, cerebral hypoxia, spinal and head trauma, and epilepsy.

A human or animal in need of a kynurenine-3-hydroxylase enzyme inhibitor can thus be treated with a method which comprises the administration thereto of a therapeutically effective amount of a compound of formula (I) or a salt thereof. The condition of the human or animal can thereby be improved.

The efficacy of the compounds of the invention in the inhibition of the enzyme kynurenine-3-hydroxylase was evaluated e.g. in rat liver mitochondrial extract following the method reported below, according to a procedure described in Analytical Biochem. (1992), 205, 257–262. The assay for kynurenine 3-hydroxylase is based on the enzymatic synthesis of tritiated water during the hydroxylation reaction. Radiolabeled water was quantified following selective adsorption of the isotopic substrate and its metabolite with activated charcoal.

Rat liver mitochondrial extract was used as enzymatic preparation for this assay.

The assay for kynurenine 3-hydroxylase activity was carried out at $37°$ C. for a time of 30 min. The reaction mixture having a total volume of 100 ml was constituted of 44 mg of suspended extract, 100 mM Tris/$Cl^-$ buffer pH 8.1, 10 mM EDTA, 100 mM KCl, 0.8 mM NADPH, 0.025 mM L-Kynurenine, 0.5 mCi L-(3,5-$^3$H)Kynurenine (10 Ci/mmol) and 10 ml of different concentration of inhibitor solutions. After the incubation, the reaction was terminated by adding 1 ml of 7.5% (W/v) activated charcoal, vortexed and centrifuged for 7 min.

A 500 ml aliquot of supernatant was counted by scintillation spectroscopy in 5 ml of liquid scintillation.

The data herewith reported in the following Table 1 clearly demonstrate the efficacy of a representative compound of the invention, namely 5-[1-benzyl-3-(3,4-dichlorophenyl)-3-oxo-propyl]-1H-tetrazole (internal code PNU-168778).

TABLE 1

| KYN-3-OH inhibition | |
|---|---|
| Compound | $IC_{50}$ |
| PNU-168778 | 2.32 $\mu$M |

The dosage level, suitable for the administration to a mammal, e.g.: to humans, depends on the age, weight, conditions of the patient and on the administration route. For example, the dosage adopted for oral administration e.g. for the representative compound of the invention PNU 168778 may range from about 10 to about 500 mg pro dose, from 1 to 5 times daily.

The compounds of formula (I) can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

The invention includes also pharmaceutical compositions comprising a compound of formula (Ia) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances conventionally used in pharmaceutical formulations. Said pharmaceutical preparations may be manufactured according to known methods, for example by means of mixing, granulating, tabletting, sugar-coating, or film-coating processes.

The liquid dispersions for oral administration may be e.g. syrups, emulsions and suspensions.

The syrups may further contain as a carrier, for example, saccharose or saccharose with glycerine and/or mannitol and/or sorbitol.

The suspensions and the emulsions may contain as a carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as a carrier, for example, sterile water or propylene glycol or, preferably, they may be in the form of sterile, aqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

With the aim of better illustrating the present invention without limiting it, the following examples are now given.

EXAMPLE 1
Preparation of (E)-2-(3,4-dichlorobenzoyl)-cyclopropylene-1-carboxamide A solution of methyl (E)-2-(3,4-dichlorobenzoyl)-cyclopropylene-1-carboxylate (3.5 9; 12.82 mmol) in 1,4-dioxane (50 ml) was treated with an ammonia solution 30% (140 ml). After 48 hours at room temperature, solvents were removed under vacuum and the resulting colourless solid was crystallised from isopropyl alcohol, yielding thus (E)-2-(3,4-dichlorobenzoyl)-cyclopropylene-1-carboxamide (2 g; 60%) (m.p. 188°–190° C.);

$^1$H-NMR (DMSO-d$^6$), δ (ppm): 8.2 (d, 1H, 2'-CH); 8.02 (dd, 1H, 6'-CH); 7.85 (d, 1H, 5'-CH); 7.75 (m, 1H, CONH); 7.12 (m, 1H, CONH); 3.15–3.02 (m, 1H, CH); 2.32–2.2 (m, 1H, CH); 1.5–1.32 (m, 2H, CH$_2$).

Analogously, the following compounds can be prepared:
4-(3-fluorophenyl)-4-oxo-butyramide;
4-(3-chlorophenyl)-4-oxo-butyramide;
4-(3-bromophenyl)-4-oxo-butyramide;
4-(3,4-dichlorophenyl)-4-oxo-butyramide;
4-(3,4-difluorophenyl)-4-oxo-butyramide.

EXAMPLE 2
Preparation of (E)-2-(3,4-dichlorobenzoyl)-cyclopropylene-1-carbonitrile p-Toluenesulfonyl chloride (2.2 g, 11.6 mmol) was added to a suspension of (E) 2-(3,4-dichlorobenzoyl)-cyclopropylene-1-carboxamide (2.0 g, 7.75 mmol) in pyridine (15 ml), maintained under magnetic stirring, and nitrogen atmosphere and the mixture was left at 80° C. for 3 hours. After cooling the reaction mixture was diluted with ethyl acetate (200 ml); the organic phase was washed with 1N hydrochloric acid (2×100 ml), potassium bicarbonate (2×100 ml), brine (2×100 ml), dried over anhydrous sodium sulphate and concentrated under vacuum. The residue was flash-chromatographed by using cyclohexane/ethyl acetate 0÷5 as eluent. (E)-2-(3,4-dichlorobenzoyl)-cyclopropylene-1-carbonitrile was yielded (1.12 g, 60%) (m.p. 86°–88° C.).

$^1$H-NMR (DMSO-d$^6$), δ (ppm): 8.38 (d, 1H, 2'-CH); 8.08 (dd, 1H, 6'-CH); 7.9 (d, 1H, 5'-CH); 3.85–3.72 (m, 1H, CH); 2.42–2.3 (m, 1H, CH); 1.75–1.48 (dm, 2H, CH$_2$).

Analogously, the following compounds can be prepared
4-(3-fluorophenyl)-4-oxo-butyronitrile;
4-(3-chlorophenyl)-4-oxo-butyronitrile;
4-(3-bromophenyl)-4-oxo-butyronitrile;
4-(3,4-dichlorophenyl)-4-oxo-butyronitrile;
4-(3,4-difluorophenyl)-4-oxo-butyronitrile.

EXAMPLE 3
Preparation of (E)-1-(3,4-dichlorobenzoyl)-2-(1H-tetrazol-5-yl)-cyclopropane (E)-2-(3,4-dichlorobenzoyl)-cyclopropylene-1-carbonitrile (1.12 g, 4.65 mmol), tri-n-butyltin azide (1.47 ml, 5.35 mmol) and toluene (25 ml) were mixed and refluxed under nitrogen atmosphere for 15 hours. The mixture was cooled, toluene was removed under vacuum and the residue was treated with 10% 1N hydrochloric acid/THF (130 ml); after 6 hours at room temperature, the reaction mixture was diluted with ethyl acetate (200 ml). The organic phase was washed with water (2×150 ml), potassium bicarbonate (2×100 ml), brine (2×150 ml), dried over anhydrous sodium sulphate and concentrated under vacuum. The residue was flash-chromatographed by using cyclohexane/ethyl acetate 0÷30 as eluent and the resulting solid was slurred with n-hexane, filtered, and dried in vacuum at 50° C. to yield (E)-1-(3,4-dichlorobenzoyl)-2-(1H-tetrazol-5-yl)-cyclopropane as a colourless solid (0.89 g, 67%) (m.p. 170°–172° C.).

$^1$H-NMR (CDCl$_3$), δ (ppm): 8.12 (d, 1H, 2'-CH); 7.86 (dd, 1H, 6'-CH); 7.58 (d, 1H, 5'-CH); 3.4 (m, 1H, CH); 3 (m, 1H, CH); 1.93 (dd, 2H, CH$_2$).

Analogously, the following compounds can be prepared:
5-[3-(3-fluorophenyl)-3-oxo-propyl]-1H-tetrazole;
5-[3-(3-chlorophenyl)-3-oxo-propyl]-1H-tetrazole;
5-[3-(3-bromophenyl)-3-oxo-propyl]-1H-tetrazole;
5-[3-(3,4-dichlorophenyl)-3-oxo-propyl]-1H-tetrazole;
5-[3-(3,4-difluorophenyl)-3-oxo-propyl]-1H-tetrazole;

5-[1-benzyl-3-(3,4-dichlorophenyl)-3-oxo-propyl]-1H-tetrazole;

1-(3,4-difluorobenzoyl)-2-(1H-tetrazol-5-yl)-cyclopropane.

EXAMPLE 4

Preparation of ethyl 2-benzyl-2-cyano-4-oxo-4-(3,4-dichlorophenyl)-butyrate

Sodium hydride (2.2 g, 46 mmol) was added to a solution of ethyl 2-cyano-3-phenyl-propionate (7.8 g, 38.4 mmol) in DMF (25 ml) maintained under magnetic stirring and nitrogen atmosphere at 0° C. The mixture was allowed to warm at room temperature and stirring was continued for 30 minutes. Then, it was cooled to 0° C. and a solution of (3,4-dichloro)-bromoacetophenone (10 g, 31 mmol) in DMF (25 ml) was dropwise added therein. After 4 hours at room temperature, the reaction mixture was quenched with water (250 ml) and extracted with ethyl acetate (3×150 ml). The organic layer was washed with brine (1×150 ml), dried over anhydrous sodium sulphate and evaporated under vacuum. The residue was flash-chromatographed by using cyclohexane/ethyl acetate 0÷30 as eluent thus affording ethyl 2-benzyl-2-cyano-4-oxo-4-(3,4-dichlorophenyl)-butyrate (8 g, 65%) (m.p. 134°–135° C.).

$^1$H-NMR (CDCl$_3$), δ (ppm): 7.95 (d, 1H, 2'-CH); 7.70 (dd, 1H, 6'-CH); 7.56 (d, 1H,5'-CH); 7.32 (m, 5H, Ph); 4.21 (m, 2H, CH$_2$); 3.55 (dd, 2H, CH$_2$Ph); 3.24 (q, 2H, CH$_2$CO); 1.2 (t, 3H, CH$_3$).

EXAMPLE 5

Preparation of 2-benzyl-2-cyano-4-oxo-4-(3,4-ichlorophenyl)-butanoic acid

A solution 1N of NaOH (36 ml, 36 mmol) was added dropwise to a solution of ethyl 2-benzyl-2-cyano-4-oxo-4-(3,4-dichlorophenyl)-butyrate (6 g, 15.4 mmol) in 95% ethanol/THF 8/1 (450 ml), maintained under magnetic stirring at 0° C. After 2 hours, the reaction mixture was poured into water (800 ml) and acidified with 37% HCl; the aqueous phase was extracted with ethyl acetate (3×300 ml). The organic extracts were washed with brine (1×400 ml), dried over anhydrous sodium sulphate and concentrated under vacuum to afford, upon treatment with n-hexane, the title compound as a colourless solid (5 g, 90%) (m.p. 181°–183° C.)

$^1$H-NMR (DMSO-d$^6$), δ (ppm): 13.79 (s, 1H, COOH); 8.21 (d, 1H, 2'-CH); 7.89 (dd, 1H, 6'-CH); 7.85 (d, 1H, 5'-CH); 7.29 (m, 5H, Ph); 3.86 (dd, 2H, CH$_2$CO); 3.20 (m, 2H, CH$_2$Ph)

EXAMPLE 6

Preparation of 2-benzyl-4-(3,4-dichlorophenyl)-4-oxo-butyronitrile

A solution of 2-benzyl-2-cyano-4-oxo-4-(3,4-dichlorophenyl)-butanoic acid (5 g, 13.8 mmol) in 10% water/1,4-dioxane (250 ml) was refluxed for about 24 hours. The solvents were removed under reduced pressure and the residue was purified by flash chromatography, using cyclohexane/ethyl acetate 0÷15 as eluent. The title compound was obtained as a colourless solid (2.7 g, 62%) (m.p. 101°–102° C.)

$^1$H-NMR (CDCl$_3$), δ (ppm): 7.97 (d, 1H, 2'-CH); 7.72 (dd, 1H, 6'-CH); 7.56 (d, 1H, 5'-CH); 7.30 (m, 5H, Ph); 3.53 (m, 1H, CH); 3.25 (dd, 2H, CH$_2$CO); 3.12 (d, 2H, CH$_2$).

EXAMPLE 7

Preparation of (E)-N-4-methoxybenzyl-4-oxo-4-(3,4-dichlorophenyl)-2-butencarboxamide A solution of 4-(3,4-dichlorophenyl)-4-oxo-2-butencarboxylic acid (2.0 g, 8.16 mmol) and oxalyl chloride (0.84 ml, 9.79 mmol) in chloroform (25 ml), was maintained at room temperature under nitrogen atmosphere for 3 hours. The solvent was removed under vacuum and the residue evaporated twice from toluene with the rotary evaporator to remove traces of oxalyl chloride. The thus obtained acid chloride was dissolved in methylene chloride (15 ml) and cooled at −78° C., under inert atmosphere. TEA (1.25 ml, 9.79 mmol), 4-DMAP (0.1 g, 0.816 mmol) and 4-methoxy benzylamine (1.12 g, 8.16 mmol) were added while magnetic stirring was continued at −78° C. for 4 hours. The reaction mixture was allowed to warm at room temperature and then diluted with methylene chloride (100 ml); the organic phase was washed with 1N HCl (3×10 ml), saturated potassium bicarbonate (3×10 ml), brine (3×15 ml), dried over anhydrous sodium sulphate and concentrated under vacuum. The residue was purified by flash chromatography, using cyclohexane/ethyl acetate 0÷5 as eluent. The title compound was obtained as a light yellow solid (1.84 g, 62w) (m.p. 169°–170° C.).

$^1$H-NMR (CDCl$_3$), δ (ppm): 8.10 (d, 1H, 2'-CH); 7.90 (d, 1H, COCH=); 7.82 (dd, 1H, 6'-CH); 7.58 (d, 1H, 5'-CH); 7.22 (d, 2H, 3", 5"-CH); 6.69 (d, 1H, =CH); 6.86 (d, 2H, 2", 6"-CH); 6.15 (m, 1H, CONH); 4.51 (d, 2H, CH$_2$); 3.80 (s, 3H, CH$_3$O).

EXAMPLE 8

Preparation of (R,S)-N-4-methoxybenzyl-2-benzyl-4-(3,4-dichlorophenyl)-4-oxo-butyramide Copper(I) bromide-dimethyl sulphide complex (0.52 g, 2.52 mmol) was added under nitrogen atmosphere to a cooled (−78° C.) solution of benzylmagnesium chloride (2M solution in THF; 3.78 ml, 7.56 mmol) in THF (30 ml). After 30 min. at −78° C. , a mixture of (E)-N-4-methoxybenzyl-4-oxo-4-(3,4-dichlorophenyl)-2-butencarboxamide (1.84 g, 5.05 mmol) and TMSC (1.28 ml, 10.1 mmol) in THF (30 ml) was added dropwise over 3 hours. Stirring was continued for one additional hour. The reaction mixture was quenched at 0° C. with a saturated aqueous NH$_4$Cl solution (10 ml). The organic layer was washed with aqueous saturated NH$_4$Cl (2×10 ml), water (2×15 ml), dried over anhydrous sodium sulphate and concentrated under vacuum. The residue was flash-chromatographed by using cyclohexane/ethyl acetate 0÷5 as eluent, thus affording the title compound as a colourless solid (1.5 g, 65%)

EXAMPLE 9

Preparation of 5-[1-benzyl-3-(3,4-dichlorophenyl)-3-oxo-propyl]-1-(4-methoxybenzyl)-1H-tetrazole (R,S)-N-(4-methoxybenzyl)-2-benzyl-4-(3,4-dichlorophenyl)-4-oxo-butyramide (1.5 9, 3.3 mmol), triphenylphosphine (1.72 g, 6.6 mmol), diethyl azidocarboxylate (1.04 ml, 6.6 mmol), trimethylsilyl azide (0.86 ml, 6.6 mmol), and THF (60 ml) were mixed and stirred at room temperature under nitrogen atmosphere for 24 hours. The mixture was cooled to 0° C. and an excess of a 5.5% aqueous solution of ammonium cerium(IV) nitrate (528 ml, 26.4 mmol) was slowly added (N$_2$ evolution). THF was then added (250 ml) too. The aqueous mixture was extracted with methylene chloride (3×400 ml). The collected organic layers were dried over anhydrous sodium sulphate, the solvent was removed under vacuum and the residue was flash-chromatographed by using cyclohexane/ethyl acetate 5÷20 as eluent. The resulting product (1.6 g) was used as such in the following step without further purification.

EXAMPLE 10

Preparation of 5-[1-benzyl-3-(3,4-dichlorophenyl)-3-oxo-propyl]-1H-tetrazole

5-[1-benzyl-3-(3,4-dichlorophenyl)-3-oxo-propyl]-1(4-methoxybenzyl)-1H-tetrazole (1.6 g, 3.3 mmol), from the previous step) and TFA (20 ml) were mixed and stirred at room temperature under nitrogen atmosphere for 40 hours. The mixture was diluted with water (100 ml) and extracted with methylene chloride (3×200 ml). The organic layers were combined, washed with water (2×100 ml), brine (1×100 ml) and dried over anhydrous sodium sulphate. The solvent was removed under vacuum and the residue was flash chromatographed by using cyclohexane/ethyl acetate 0÷20 as eluent. The title compound was obtained as a colourless solid (0.6 g, 50%) (m.p. 172°–174° C.).

$^1$H-NMR (CDCl$_3$) δ (ppm): 7.96 (d, 1H, 2'-CH); 7.68 (dd, 1H, 6'-CH); 7.53 (d, 1h, 5'-CH); 7.32–7.12 (m, 5H, Ph); 4 (m, 1H, CH); 3.64 (dd, 1H, CHPh); 3.36 (dd, 1H, CHPh); 3.28–3.15 (m, 2H, COCH$_2$).

EXAMPLE 11

Capsules, each weighing 0.23 g and containing 50 mg of the active substance, can be prepared as follows:

Composition for 500 capsules:

| | |
|---|---|
| (E)-1-(3,4-dichlorobenzoyl)-2-(1H-tetrazol-5-yl)-cyclopropane | 25 g |
| Lactose | 80 g |
| Corn starch | 5 g |
| Magnesium stearate | 5 g |

This formulation can be encapsulated into hard gelatine capsules of two pieces, each capsule weighing 0.23 g.

EXAMPLE 12

Intramuscular Injection of 50 mg/ml

A pharmaceutical injectable composition can be manufactured by dissolving 50 g of 5-[3-(3,4-dichlorophenyl)-3-oxo-propyl]-1H-tetrazole in sterile propylene glycol (1000 ml) and sealed in 1–5 ml ampoules.

Legend to FIG. 1
IDO=Indolamineoxigenase
KYN=Kynurenine
KYN-OH=Kynurenine-3-hydroxylase
KYNA=Kynurenic acid
3-OHAA=3-hydroxy anthranilic acid
KYNase=Kynureninase
QUIN=Quinolinic acid
3-HAO=3-hydroxy anthranilic acid deoxygenase
KAT=kynurenine amino transferase
3-OHKYN=3-Hydroxy-kynurenine

What is claimed is:

1. A compound which is a 5-(3-phenyl-3-oxo-propyl)-1H-tetrazole derivative of formula (I)

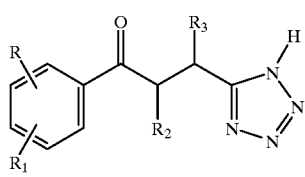

(I)

wherein
each of R and R$_1$, being the same or different, is hydrogen, halogen, hydroxy, trifluoromethyl, cyano, nitro, phenyl, benzyl, C$_1$–C$_6$ alkyl, C$_1$–C$_6$ alkoxy, C$_1$–C$_6$ alkylthio, SOR$_4$ or SO$_2$R$_4$ wherein R$_4$ is C$_1$–C$_6$ alkyl, or —N(R$_5$R$_6$) in which each of R$_5$ and R$_6$ is, independently, hydrogen, C$_1$–C$_6$ alkyl, formyl or C$_2$–C$_6$ acyl;
R$_2$ is hydrogen, C$_1$–C$_6$ alkyl, C$_1$–C$_6$ alkoxy, benzyl, or phenyl;
R$_3$ is hydrogen, hydroxy, C$_1$–C$_6$ alkyl, C$_1$–C$_6$ alkoxy, benzyl, phenyl or a group —N(R$_7$R$_8$) in which each of R$_7$ and R$_8$ is, independently, hydrogen, C$_1$–C$_4$ alkyl, benzyl, or phenyl, or one of R$_7$ and R$_8$ is hydrogen and the other is COR$_9$ wherein R$_9$ is hydrogen, C$_1$–C$_4$ alkyl, C$_1$–C$_4$ alkoxy, phenyl or a group —N(R$_{10}$R$_{11}$) in which R$_{10}$ and R$_{11}$ are, each independently, hydrogen or C$_1$–C$_4$ alkyl or, taken together, R$_2$ and R$_3$ form a carbocyclic C$_3$–C$_6$ ring, or a pharmaceutically acceptable salt thereof.

2. A compound which is a 5-(3-phenyl-3-oxo-propyl)-1H-tetrazole derivative of formula (Ia)

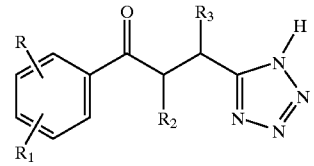

(Ia)

wherein
each of R and R$_1$, being the same or different, is hydrogen, halogen, trifluoromethyl, cyano, nitro, benzyl, C$_1$–C$_6$ alkylthio, SOR$_4$ or SO$_2$R$_4$ in which R$_4$ is C$_1$–C$_6$ alkyl, or —N(R$_5$R$_6$) in which each of R$_5$ and R$_6$ is, independently, hydrogen, C$_1$–C$_6$ alkyl, formyl or C$_2$–C$_6$ acyl;
R$_2$ is hydrogen, C$_1$–C$_6$ alkyl, C$_1$–C$_6$ alkoxy, benzyl, or phenyl;
R$_3$ is hydrogen, hydroxy, C$_1$–C$_6$ alkyl, C$_1$–C$_6$ alkoxy, benzyl, phenyl or a group —N(R$_7$R$_8$) in which each of R$_7$ and R$_8$ is, independently, hydrogen, C$_1$–C$_4$ alkyl, benzyl, or phenyl, or one of R$_7$ and R$_8$ is hydrogen and the other is COR$_9$ wherein R$_9$ is hydrogen, C$_1$–C$_4$ alkyl, C$_1$–C$_4$ alkoxy, phenyl or a group —N(R$_{10}$R$_{11}$) in which R$_{10}$ and R$_{11}$ are, each independently, hydrogen or C$_1$–C$_4$ alkyl or, taken together, R$_2$ and R$_3$ form a carbocyclic C$_3$–C$_6$ ring; or a pharmaceutically acceptable salt thereof a racemic mixture or an individual optical isomer; and/or an individual geometric (E) or (Z) isomer or a mixture of such isomer.

3. A compound according to claim 2 wherein each of R and R$_1$, being the same or different, is hydrogen, halogen, or trifluoromethyl; R$_2$ is hydrogen, C$_1$–C$_4$ alkyl, C$_1$–C$_6$ alkoxy, benzyl, or phenyl; R$_3$ is hydrogen, hydroxy, C$_1$–C$_6$ alkyl, C$_1$–C$_6$ alkoxy, benzyl, phenyl or a group —N(R$_7$R$_8$) in which each of R$_7$ and R$_8$ is, independently, hydrogen, C$_1$–C$_4$ alkyl, benzyl, or phenyl, or one of R$_7$ and R$_8$ is hydrogen and the other is COR$_9$ wherein R$_9$ is hydrogen, C$_1$–C$_4$ alkyl, C$_1$–C$_4$ alkoxy, phenyl or a —N(R$_{10}$R$_{11}$) group in which R$_{10}$ and R$_{11}$ are, each independently, hydrogen or C$_1$–C$_4$ alkyl or, taken together, R$_2$ and R$_3$ form a carbocyclic C$_3$–C$_6$ ring; or a pharmaceutically acceptable salt thereof.

4. A compound according to claim 2 wherein R and R$_1$ are both halogen atoms.

5. A compound according to claim 2 selected from:

5-[3-(3-fluorophenyl)-3-oxo-propyl]-1H-tetrazole;

5-[3-(3-chlorophenyl)-3-oxo-propyl]-1H-tetrazole;

5-[3-(3-bromophenyl)-3-oxo-propyl]-1H-tetrazole;

5-[3-(3,4-dichlorophenyl)-3-oxo-propyl]-1H-tetrazole;

5-[3-(3,4-difluorophenyl)-3-oxo-propyl]-1H-tetrazole;

5-[1-benzyl-3-(3,4-dichlorophenyl)-3-oxo-propyl]-1H-tetrazole;

1-(3,4-dichlorobenzoyl)-2-(1H-tetrazol-5-yl)-cyclopropane;

1-(3,4-difluorobenzoyl)-2-(1H-tetrazol-5-yl)-cyclopropane; or a pharmaceutically acceptable salt thereof; a racemic mixture or an individual optical isomer; and/or an individual geometric (E) or (Z) isomer or a mixture of such isomer.

6. A pharmaceutical composition which comprises a pharmaceutically acceptable carrier or diluent and, as an active ingredient, a therapeutically effective amount of a compound as defined in claim 2.

7. A process for producing a compound as defined in claim 2, which process comprises:

a) reacting a compound of formula (II)

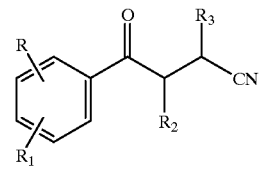

(II)

wherein R, $R_1$, $R_2$ and $R_3$ are as defined in claim 2, with a trialkyl tin azide, or, b) reacting a compound of formula (III)

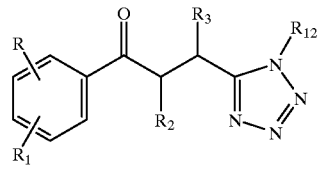

(III)

wherein R, $R_1$, $R_2$ and $R_3$ are as defined in claim 2 and $R_{12}$ is a substituted benzyl group, with a hydrolysing agent; and, (c) if desired, converting a compound of formula (Ia) into a pharmaceutically acceptable salt thereof.

* * * * *